United States Patent [19]
Augustine et al.

[11] Patent Number: 5,256,163
[45] Date of Patent: Oct. 26, 1993

[54] FLOW LIQUID-PHASE CHEMICAL REACTION PROCESS

[75] Inventors: Robert L. Augustine, Livingston; Glen Wolosh, Randolph, both of N.J.

[73] Assignees: Philip Morris Incorporated, New York, N.Y.; Philip Morris Products Inc., Richmond, Va.

[21] Appl. No.: 757,563

[22] Filed: Sep. 11, 1991

[51] Int. Cl.$^5$ ............................ B01J 8/08; C07C 5/05; C07C 67/00
[52] U.S. Cl. .................... 422/232; 585/271; 585/273; 585/274; 585/275; 560/131
[58] Field of Search ............... 422/188, 190, 192, 213, 422/232, 233, 236, 261, 242; 585/271, 274, 250, 273, 275, 652, 653; 560/131

[56] References Cited

U.S. PATENT DOCUMENTS

| | | | |
|---|---|---|---|
| 2,882,319 | 4/1959 | Hotelling et al. | 422/190 |
| 4,191,839 | 3/1980 | Lyons et al. | 560/131 |
| 4,260,808 | 4/1981 | Lyons et al. | 560/131 |
| 4,332,963 | 6/1982 | Lyons et al. | 560/131 |
| 4,691,069 | 9/1987 | Albers et al. | 585/273 |
| 4,691,070 | 9/1987 | Nakamura et al. | 585/273 |
| 4,705,906 | 11/1987 | Brophy et al. | 585/273 |
| 4,716,256 | 12/1987 | Johnson et al. | 585/274 |
| 4,748,290 | 5/1988 | Cymbaluk | 585/271 |
| 5,171,911 | 12/1992 | Tour et al. | 585/273 |

*Primary Examiner*—Robert J. Warden
*Assistant Examiner*—Christopher Y. Kim
*Attorney, Agent, or Firm*—James E. Schardt

[57] ABSTRACT

The present invention provides a flow liquid-phase chemical reaction system in which a high pressure reservoir unit holds a solvent solution which contains an organic reactant and a gas reactant. The quantity of gas reactant dissolved in the solvent solution is determined by the level of gas reactant vapor pressure in the reservoir unit. The solvent solution is passed through a solid catalyst reactor unit to achieve a selective reaction between the two reactant components of the solvent solution.

5 Claims, 2 Drawing Sheets

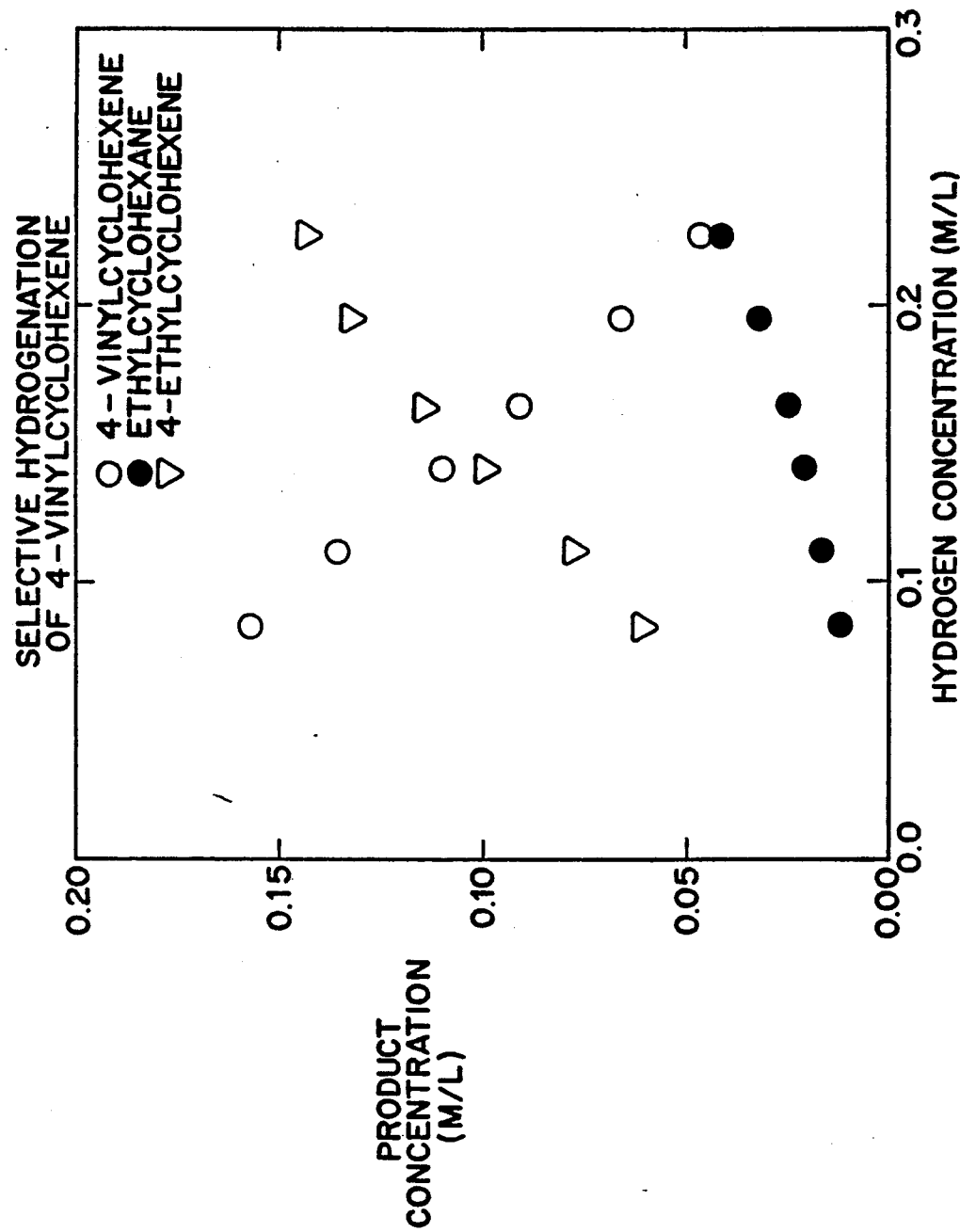

FLOW LIQUID-PHASE CHEMICAL REACTION PROCESS

BACKGROUND OF THE INVENTION

Selective reactions involving gaseous reagents such as catalytic hydrogenation or oxygenation typically are conducted in either a flow system or a batch reactor. In a flow system the reaction can be run in the vapor phase or in the liquid phase, while in a batch process only liquid phase reactions are feasible. Vapor phase conditions are suitable for selective reactions, but are limited by the volatility and temperature stability of the reactants and products. Liquid phase reactions have a more general application.

In a selective liquid phase reaction such as the hydrogenation of a diene or acetylene to a monoene, the reactant is dissolved in a solvent and either stirred with the catalyst under an atmosphere of hydrogen (batch mode) or passed through a bed of catalyst while in contact with hydrogen gas. In either mode the reaction selectivity is influenced primarily by the nature of the catalyst. The desired monoene is produced because of a preferential adsorption on the catalyst of the reacting diene or acetylene which displaces the monoene before complete saturation can occur.

Hydrogen availability to the catalyst also affects this type of reaction selectivity in that the desorption of the monoene will be favored over its saturation when a limited amount of hydrogen is available to the catalyst. In both flow and batch reactors hydrogen availability is determined by the extent of gas/liquid diffusion of the hydrogen, and is controlled by varying the hydrogen pressure, rate of agitation, degree of hydrogen sparging, and the like. The degree of hydrogen availability control by these means is limited, so that invariably the hydrogen is present in large excess over the organic reactant substrate, and reaction selectivity is controlled primarily by the properties of the catalyst.

In many cases extensive preparation procedures are required to modify a catalyst in order to obtain the desired selectivity. This is illustrated by the selective hydrogenation of 4-vinylcyclohexene to 4-ethylcyclohexene with a nickel boride catalyst or a nickel arsenide catalyst prepared by the reduction of nickel arsenate with sodium borohydride in the presence of either silica or alumina as described in references such as J. Am. Chem. Soc., 85, 1005 (1963); J. Org. Chem., 38, 2226 (1973); and U.S. Pat. No. 4,716,256; 4,659,687; and 4,748,290. These catalysts generally provide about a 50% selectivity at 75-100% conversion. Treatment of an arsenide catalyst with ammonia increases the selectivity to 83% at 72% conversion. When the hydrogenation reaction is conducted in the presence of acetone over an alumina supported arsenide catalyst, a 96% selectivity at 96% conversion is obtained. Overreduction of an arsenide catalyst results in a reactivity which favors double bond isomerization. (J. Catal., 27, 397 (1972) reports that overreduced catalyst yields only about a 10% selectivity at 95% conversion, and the main product consists of double bond isomers.

There is continuing interest in chemical reaction systems for improved selective conversion of organic compounds.

Accordingly, it is an object of this invention to provide a flow liquid-phase chemical reaction system for selective conversion of organic compounds with a gas reactant.

It is a further object of this invention to provide a chemical reaction system with novel means for control of the molar ratio of gas reactant and organic compound dissolved in a solvent medium flowing through a catalyst bed.

Other objects and advantages of the present invention shall become apparent from the accompanying example and drawings.

DESCRIPTION OF THE INVENTION

One or more objects of the present invention are accomplished by the provision of a flow liquid-phase chemical reaction system comprising:

(a) a high pressure reservoir unit containing a solvent solution of an organic reactant and a gas reactant, wherein the reservoir unit is under gas reactant pressure which provides a calculated molar ratio of gas reactant saturation to organic reactant in the solvent solution; and (b) a solid catalyst reactor unit which is connected to the high pressure reservoir unit;

wherein during an operating cycle the solvent solution is passed from the reservoir unit through the reactor unit under controlled flow rate, temperature and pressure conditions, and a product solution stream is obtained from the reactor unit.

The invention flow liquid-phase chemical reaction system has particular advantage for a reaction in which hydrogenation or oxygenation of an organic compound requires a controlled molar ratio of hydrogen or oxygen reactant to organic compound reactant in order to achieve an efficient level of conversion selectivity.

The solvent employed in the high pressure reservoir unit is inert under the particular reaction conditions, and has sufficient solvating power to dissolve both the gas reactant and the organic compound reactant, and the products of the reaction. Suitable solvents include methanol, ethanol, acetone, diethyl ether, tetrahydrofuran, N-dimethylformamide, dimethyl sulfoxide, benzene, toluene, nitrobenzene, carbon tetrachloride, carbon disulfide, ethyl acetate, and the like.

The gas reactant pressure in the reservoir unit is maintained at a level between about 50-2000 psi which provides the desired molar content of dissolved gas reactant saturation in the solvent solution relative to the organic compound reactant.

The organic compound reactant preferably is one which requires controlled reaction conditions in order to accomplish an efficient selective reaction with the gas reactant. The present invention reaction system is adapted to hydrogenate dienes and acetylenes to monoenes, or acylate a benzyl or allylic carbon position under oxygenation conditions.

The transfer of the solvent solution from the reservoir unit to the solid catalyst reactor unit is conducted with a flow rate which in combination with the specific reactor temperature and pressure and catalyst favors an optimal conversion to the desired product. The flow rate for a laboratory scale reaction system typically will be in the range between about 0.5-10 millimeters per minute when the solvent solution contains between about 1-10 percent of organic compound reactant.

The reactor unit contains a bed of a solid catalyst which is suitable for the particular reaction being conducted. Because the present invention system achieves reaction selectivity primarily by control of the gas reactant availability, it is not necessary to employ any specially prepared or modified catalyst. The present reaction system operates efficiently with conventional commercial catalysts such as a particulate group IV-VIII metal either alone or in combination with other metals. The metal catalyst can be utilized in combination with a support substrate such as alumina, titania, silica, magnesia, zeolites, and the like.

The pressure in the reactor unit is provided at a level which is at least sufficient to maintain the gas reactant saturation in the solvent solution. The selected reactor temperature generally will be in the range between about 25°-200° C. as appropriate for the contemplated catalytic reaction conditions.

The advantages of the present invention reaction system derive mainly from the means for control of gas reactant availability in the catalytic reaction zone. There is no gas/liquid interface within the reaction zone. The reaction selectively is regulated by the quantity of gas reactant dissolved in the flowing solvent solution feedstream.

BRIEF DESCRIPTION OF THE DRAWINGS

Specific embodiments of the present invention are illustrated in the following example and drawings.

FIG. 2 is a graphic representation of the hydrogenation of 4-vinylcyclohexene over 5% platinum-on-carbon catalyst as described in the Example.

EXAMPLE

Figure 1:
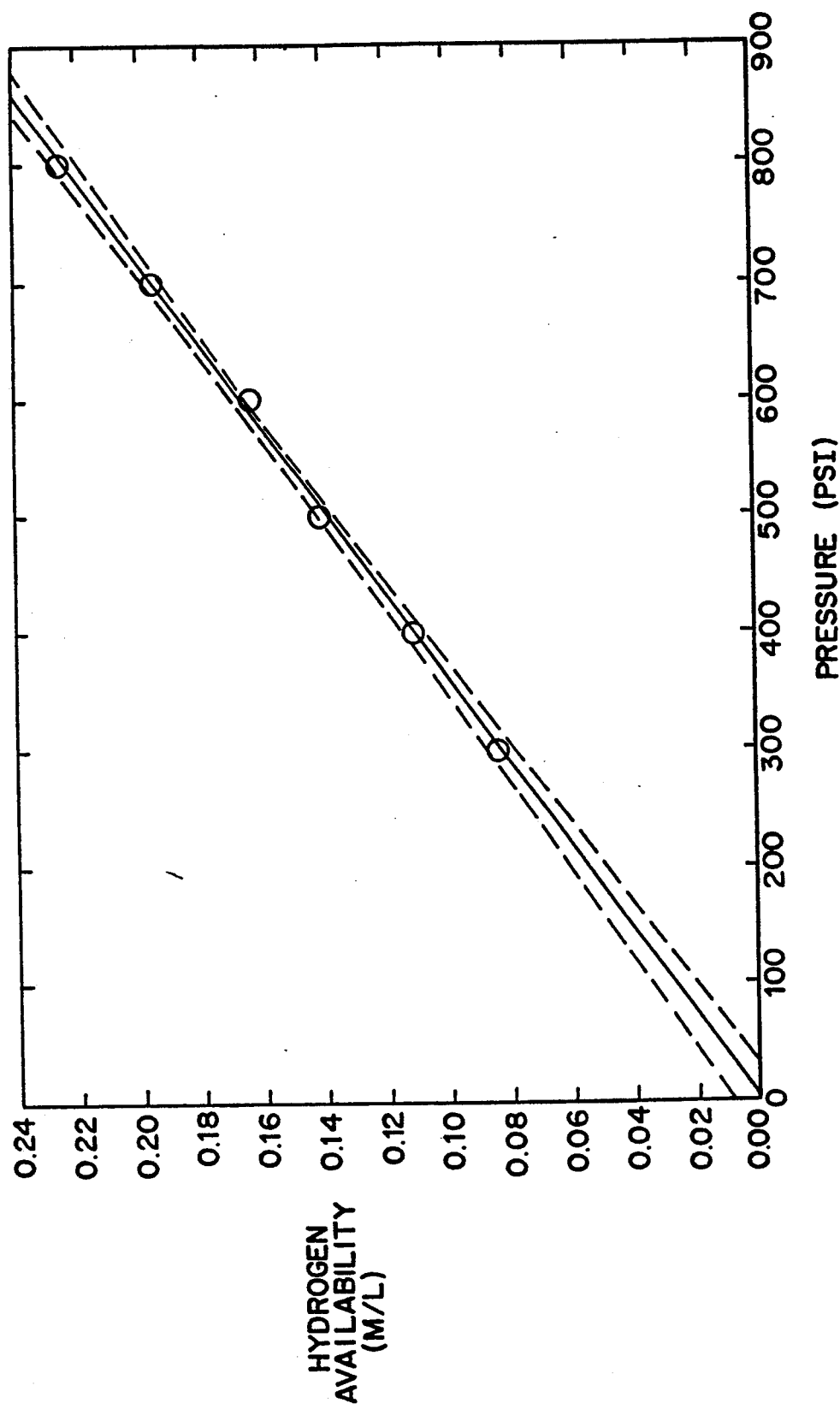
FIG. 1 is a graphic representation of a gas solubility/pressure plot for the solubility of hydrogen in methanol. The hydrogen availability axis in FIG. 1 corresponds to the hydrogen concentration axis in FIG. 2.

This Example illustrates selective hydrogenation and selective oxygenation reactions employing a present invention flow liquid-phase chemical reaction system.

A. Hydrogenation

A 3% solution of 4-vinylcyclohexene is prepared by admixing 15 mL of 4-vinylcyclohexene with methanol to form a 500 mL solution.

A catalyst bed is prepared by the following procedure. Glass beads (Alltech Associates, 125/100 mesh, DMCS treated, 3.65 g) and catalyst (Engelhard 5% Pt/C, 0.3 g) are shaken together in a vial until well mixed. An empty HPLC column (150 mm x 4.6 mm) is packed with the glass bead/catalyst mixture, and the column temperature is controlled at 30° C. (MGW Lauda MT water bath).

The 4-vinylcyclohexene solution is charged to a stainless steel bomb (500 mL, Parr 4762 GP 316) which functions as a reservoir unit for the solvent solution. The bomb is pressured with hydrogen to 300 psi. The flow rate is set at 1 mL/minute with a pump (DuPont 870), and the reaction is allowed to proceed, and product stream samples are collected and analyzed by GC (Hewlett Packard 5890 Gas Chromatograph).

The reaction is repeated at pressures of 400, 500, 600, 700 and 800 psi, respectively. The reactor pressure is controlled with two flow restrictors (Rainen 500 psi) in tandem.

The results of the six hydrogenation reaction runs are summarized in FIG. 2. The graphic representation illustrates that the invention reaction system provides a selective high yield of 4-ethylcyclohexene as compared with the low yield of ethylcyclohexane byproduct. There is an 80% selectivity at 80% conversion.

B. Oxygenation

A selective oxygenation reaction is performed in the same reaction system as employed for the hydrogenation reaction.

Oxygen is employed as the gas reactant, and the solid catalyst in the reactor unit is a particulate palladium-tin (1:2)/Fluorosil bed.

The solvent solution consists of toluene and acetic acid, and dissolved oxygen.

The reaction is conducted with a reactor unit temperature of 70° C. GC analysis of the product solution stream indicates that the toluene starting material is acetoxylated selectively to benzyl acetate and benzylidene diacetate in a molar ratio of about 3:1.

What is claimed is:

1. A flow liquid-phase chemical reaction process for hydrogenation or oxygenation of organic compounds which comprises (a) charging a reservoir container unit with a solvent solution of an organic reactant; (b) pressuring the reservoir unit with hydrogen or oxygen gas reactant to provide a controlled molar ratio of dissolved gas reactant saturation to organic reactant in the solvent solution; (c) passing the saturated solvent solution from the reservoir unit through a solid catalyst reaction unit under controlled flow rate, temperature and pressure conditions; and (d) recovering a hydrogenated or oxygenated organic product solution stream from the reactor unit.

2. A chemical reaction process in accordance with claim 1 wherein the gas reactant is hydrogen.

3. A chemical reaction process in accordance with claim 1 wherein the gas reactant is oxygen.

4. A chemical reaction process in accordance with claim 1 wherein (1) the gas reactant is hydrogen, (2) the solvent solution contains 4-vinylcyclohexene, and (3) the reactor contains a hydrogenation catalyst, and wherein the product solution stream contains 4-ethylcyclohexene product.

5. A chemical reaction process in accordance with claim 1 wherein (1) the gas reactant is oxygen, and (2) the solvent solution contains a carboxylic acid component and an organic compound component with an allylic carbon position having at least one hydrogen substituent, and wherein the product solution stream contains an organic compound product with an acetoxylated allylic carbon position.

* * * * *